(12) United States Patent
Jo et al.

(10) Patent No.: US 12,276,554 B2
(45) Date of Patent: Apr. 15, 2025

(54) ELECTRONIC DEVICE INCLUDING A PLURALITY OF TEMPERATURE SENSORS

(71) Applicant: SAMSUNG ELECTRONICS CO., LTD., Suwon-si (KR)

(72) Inventors: Seongwook Jo, Suwon-si (KR); Injo Jeong, Suwon-si (KR); Hyunguk Yoo, Suwon-si (KR); Jeahyuck Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 100 days.

(21) Appl. No.: 18/078,388

(22) Filed: Dec. 9, 2022

(65) Prior Publication Data

US 2023/0184599 A1 Jun. 15, 2023

Related U.S. Application Data

(63) Continuation of application No. PCT/KR2022/020029, filed on Dec. 9, 2022.

(30) Foreign Application Priority Data

Dec. 9, 2021 (KR) .................. 10-2021-0175645
Mar. 7, 2022 (KR) .................. 10-2022-0028761

(51) Int. Cl.
*G01K 13/20* (2021.01)
*A61B 5/00* (2006.01)
(Continued)

(52) U.S. Cl.
CPC .............. *G01K 13/223* (2021.01); *A61B 5/01* (2013.01); *A61B 5/681* (2013.01); *G01J 5/58* (2013.01);
(Continued)

(58) Field of Classification Search
CPC .......... G01K 13/223; G01K 7/22; A61B 5/01; A61B 5/681; A61B 2560/0252;
(Continued)

(56) References Cited

U.S. PATENT DOCUMENTS 10,168,219 B2  1/2019  Sun et al.
11,109,764 B2  9/2021  Bongers et al.
(Continued)

FOREIGN PATENT DOCUMENTS

CN  109655177 A  4/2019
CN  112050950    12/2020
(Continued)

OTHER PUBLICATIONS

Search Report and Written Opinion dated Mar. 16, 2023 issued in International Patent Application No. PCT/KR2022/020029.
(Continued)

*Primary Examiner* — Sean A Frith
(74) *Attorney, Agent, or Firm* — Nixon & Vanderhye P.C.

(57) ABSTRACT

According to various embodiments, a wearable electronic device may include: a housing comprising a first plate including a first surface facing in a first direction, and a second plate including a second surface facing a second direction opposite to the first direction; a substrate disposed in a space between the first plate and the second plate of the housing; a processor; and at least two temperature sensors, wherein the at least two temperature sensors comprise a contact-type temperature sensor and a non-contact-type temperature sensor arranged at positions different from each other in the housing, and the processor is configured to: determine a body temperature using the temperatures measured by the contact-type temperature sensor and the non-contact-type temperature sensor.

20 Claims, 7 Drawing Sheets

(51) Int. Cl.
*A61B 5/01* (2006.01)
*G01J 5/58* (2022.01)
*G01K 7/22* (2006.01)

(52) U.S. Cl.
CPC ........ *G01K 7/22* (2013.01); *A61B 2560/0252* (2013.01); *A61B 2562/0271* (2013.01); *A61B 2562/063* (2013.01); *A61B 2562/164* (2013.01)

(58) Field of Classification Search
CPC ...... A61B 2562/0271; A61B 2562/063; A61B 2562/164; G01J 5/58
See application file for complete search history.

(56) References Cited

U.S. PATENT DOCUMENTS

| | | | |
|---|---|---|---|
| 2008/0171920 A1* | 7/2008 | Teller | A63B 24/0062 600/301 |
| 2010/0217099 A1* | 8/2010 | LeBoeuf | A61B 5/6815 600/301 |
| 2014/0207045 A1 | 7/2014 | Heller | |
| 2014/0207405 A1 | 7/2014 | Heller | |
| 2019/0090806 A1 | 3/2019 | Clavelle et al. | |
| 2019/0350462 A1* | 11/2019 | Biederman | G01K 7/42 |
| 2020/0401183 A1 | 12/2020 | von Badinski et al. | |
| 2022/0386878 A1* | 12/2022 | Li | G01J 5/064 |

FOREIGN PATENT DOCUMENTS

| | | |
|---|---|---|
| JP | 2016-144560 | 8/2016 |
| JP | 2016-206024 | 12/2016 |
| KR | 10-1885902 | 8/2018 |
| KR | 10-2019-0061772 | 6/2019 |
| KR | 10-2125070 | 6/2020 |
| KR | 10-2021-0029625 A | 3/2021 |
| WO | 2021/057873 | 4/2021 |

OTHER PUBLICATIONS

Huang et al., "Wearable Deep Body Thermometers and Their Uses in Continuous Monitoring for Daily Healthcare", 2016 38th Annual International Conference of the IEEE Engineering in Medicine and Biology Society (EMBC), pp. 177-180, Aug. 20, 2016, 5 pages.
Lazaro et al., "Smart Face Mask with an Integrated Heat Flux Sensor for Fast and Remote People's Healthcare Monitoring", Sensors, vol. 21, Issue 22, Nov. 10, 2021, 28 pages.
European Search Report dated Sep. 6, 2024 for EP Application No. 22904714.7.

* cited by examiner

ELECTRONIC DEVICE INCLUDING A PLURALITY OF TEMPERATURE SENSORS

CROSS-REFERENCE TO RELATED APPLICATIONS

This application is a continuation of International Application No. PCT/KR2022/020029 designating the United States, filed on Dec. 9, 2022, in the Korean Intellectual Property Receiving Office and claiming priority to Korean Patent Application No. 10-2021-0175645, filed on Dec. 9, 2021, in the Korean Intellectual Property Office, and to Korean Patent Application No. 10-2022-0028761, filed on Mar. 7, 2022, in the Korean Intellectual Property Office, the disclosures of all of which are incorporated by referenced herein in their entireties.

BACKGROUND

Field

The disclosure relates to an electronic device including multiple temperature sensors.

Description of Related Art

In general, electronic devices refer to device configured to perform specific functions according to installed programs, such as home appliances, electronic diaries, portable multimedia players, mobile communication terminals, tablet PCs, video/audio devices, desktop/laptop computers, and vehicle navigation systems. Such electronic devices may output stored information as sounds or images. In line with the high degree of integration of electronic devices and the widespread use of super-fast large-capacity wireless communication, it has recently become possible to equip a single mobile communication terminal with various functions. Not only a communication function, but also an entertainment function (for example, gaming), a multimedia function (for example, music/video playback), communication and security functions for mobile banking, a scheduling function, and an electronic wallet function may be integrated into a single electronic device.

Wearable electronic devices have been disclosed in various types, such as eyeglasses or watches, such that electronic devices can be mounted on human bodies and used. It has recently been requested to integrate various functions in wearable electronic devices, as in the case of mobile communication terminals.

A wearable electronic device may include at least one sensor for acquiring a user's biometric information, based on the fact that the same is mounted on a human body. For example, the wearable electronic device may include at least one sensor capable of acquiring biometric information such as the user's ECG, breathing, EMG, EOG, EEG, blood glucose, SpO2, PPG, or body temperature.

In connection with designing a wearable electronic device having a limited space to arrange components, it may be important to arrange various components in adequate positions. In addition, when a wearable electronic device is equipped with a sensor capable of acquiring biometric information, it may be critical to secure the reliability of the sensor through accurate calibration.

When mounted on a wearable electronic device as a sensor for acquiring the user's biometric information, a body temperature sensor may sense the user's body temperature while making close contact with the user's skin. According to the prior art, a contact-type body temperature sensor and a non-contact-type body temperature are disclosed as body temperature sensors mounted on wearable electronic devices. The contact-type body temperature sensor may measure the user's body temperature using a thermistor, the resistance of which is changed sensitively by a temperature change, for example. The non-contact-type body temperature sensor may detect thermal energy radiated from the skin, for example, using an infrared (IR) absorber, and may estimate the user's body temperature, based thereon, using the Stefan-boltzman formula.

The non-contact-type body temperature sensor may have a more complicated structure and a higher manufacturing cost than the contact-type body temperature sensor. The contact-type body temperature sensor may have a simpler structure and a lower manufacturing cost than the non-contact-type body temperature sensor, but is vulnerable to influences of external environments, and the measured body temperature result may thus be inaccurate.

SUMMARY

According to various example embodiments of the disclosure, a wearable electronic device may include: a housing comprising a first plate including a first surface facing in a first direction, and a second plate including a second surface facing a second direction opposite to the first direction; a substrate disposed in a space between the first plate and the second plate of the housing; a processor; and at least two temperature sensors, wherein the at least two temperature sensors include a contact-type temperature sensor and a non-contact-type temperature sensor arranged at positions different from each other in the housing, and wherein the processor is configured to: determine a body temperature using the temperatures measured by the contact-type temperature sensor and the non-contact-type temperature sensor.

According to various example embodiments of the disclosure, a method for measuring a body temperature using a wearable electronic device including a contact-type temperature sensor and a non-contact-type temperature sensor may include: measuring a temperature of a first point using the contact-type temperature sensor and measuring, using the non-contact-type temperature sensor, a temperature of a second point disposed to be spaced apart from the first point by a specified distance in a height direction of the wearable electronic device, to monitor a heat flow information; and determining a body temperature, based on both accumulated data on the temperature estimated through monitoring the heat flow information and temperature data immediately measured through the non-contact-type temperature sensor.

According to various example embodiments of the disclosure, an electronic device may include: a housing; a substrate disposed inside the housing; a processor; and at least two temperature sensors, wherein the at least two temperature sensors include a contact-type temperature sensor and a non-contact-type temperature sensor arranged at positions different from each other in the housing, and the processor is configured to: determine a body temperature using the temperatures measured by the contact-type temperature sensor and the non-contact-type temperature sensor.

An electronic device according to various example embodiments of the disclosure may use a contact-type body temperature sensor and a non-contact-type body temperature sensor in a combined manner, thereby performing accurate body temperature measurements in various use environments.

According to various example embodiments of the disclosure, and a non-contact-type body temperature sensor is used to instantly measure the temperature, thereby acquiring real-time data, and accumulated data regarding temperatures acquired by a contact-type body temperature sensor and a non-contact-type body temperature sensor is acquired and is compensated for based thereon such that body temperatures can be measured more accurately.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
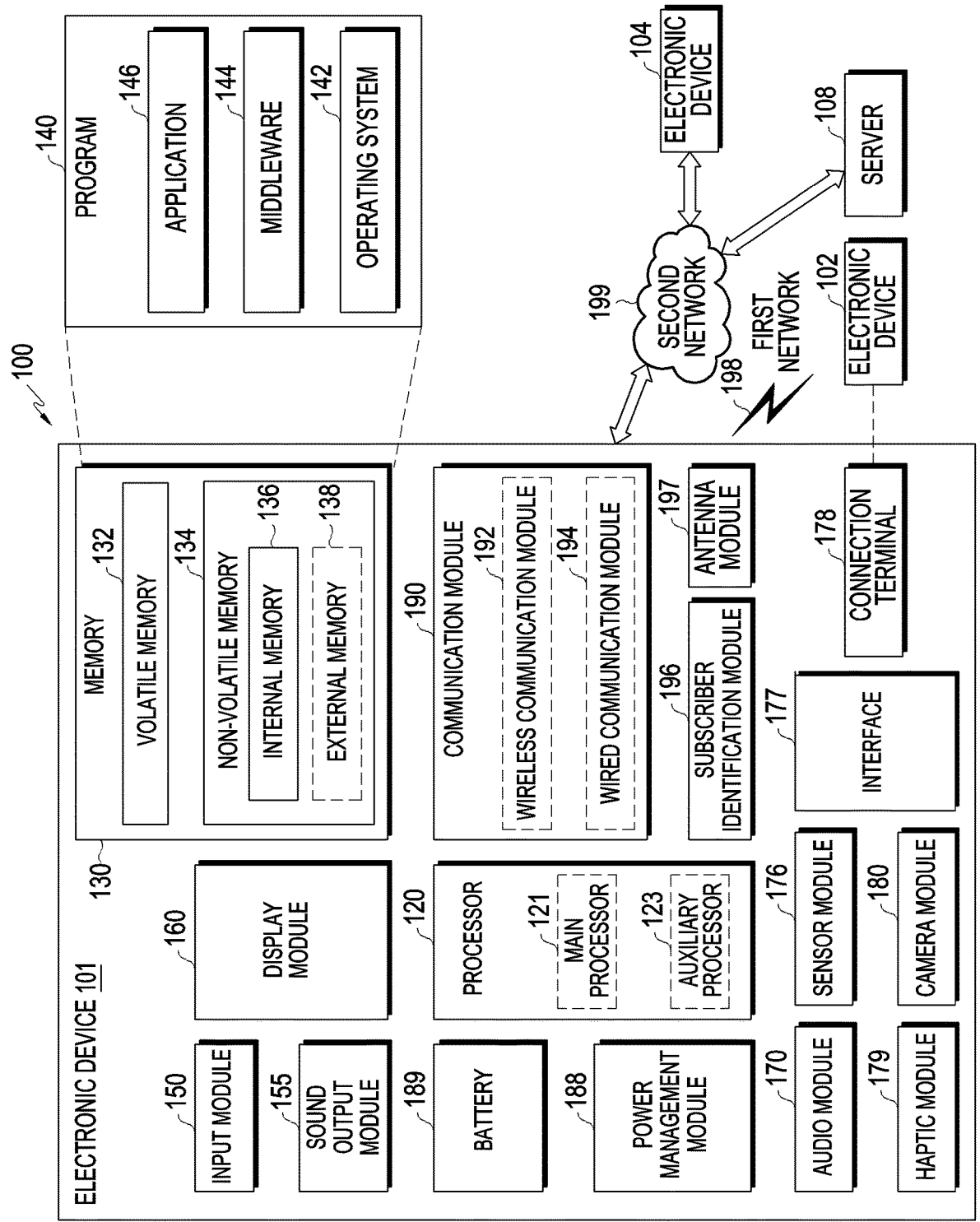
FIG. 1 is a block diagram illustrating an example electronic device in a network environment according to various embodiments.

FIG. 1 is a block diagram illustrating an example electronic device 101 in a network environment 100 according to various embodiments. Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In various embodiments, at least one of the components (e.g., the connecting terminal 178) may be omitted from the electronic device 101, or one or more other components may be added in the electronic device 101. In various embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control, for example, at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence model is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or an external electronic device (e.g., an electronic device 102 (e.g., a speaker or a headphone)) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element including a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, an RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the external electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In an embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
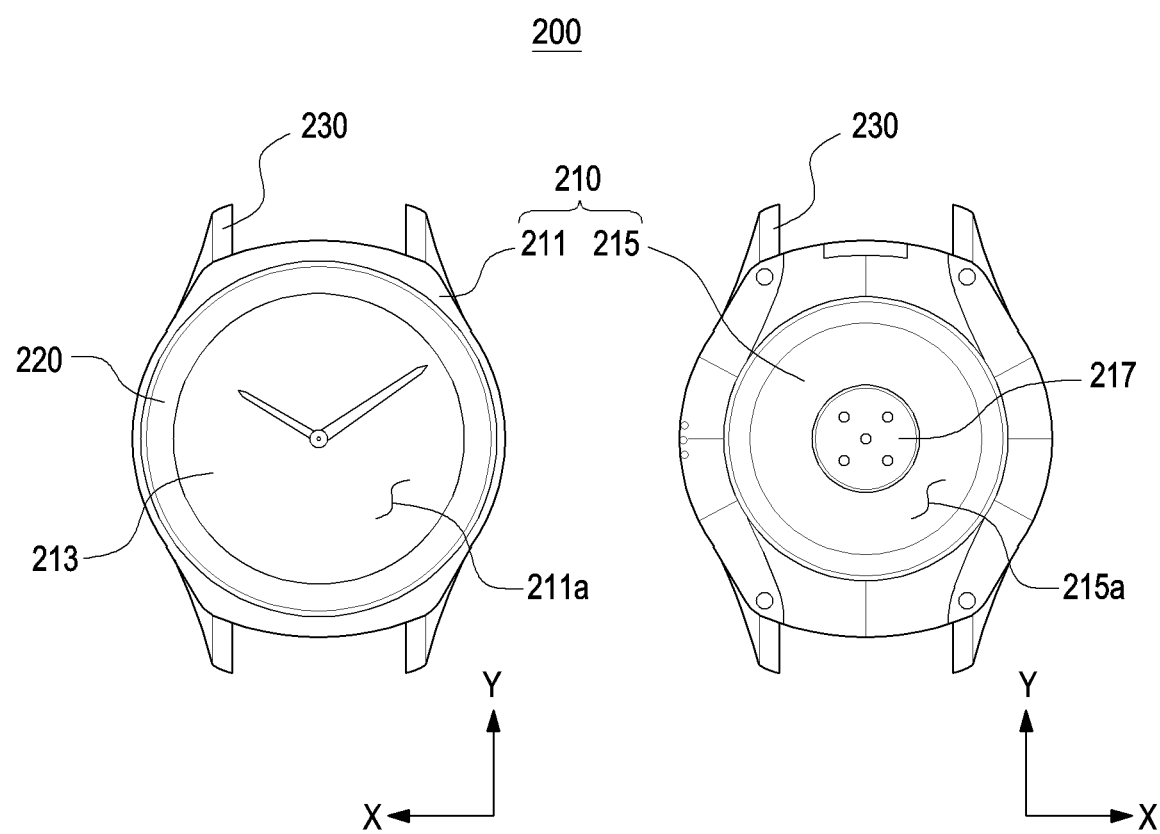
FIG. 2 is a diagram illustrating an example electronic device according to various embodiments.

FIG. 2 is a diagram illustrating an example electronic device according to various embodiments. FIG. 2 shows a front view and a rear view of an electronic device.

In the following detailed descriptions, a longitudinal direction, a width direction, and/or a height direction (a thickness direction) of an electronic device 200 may be mentioned, the longitudinal direction may refer to the "Y-axis direction", the width direction may refer to the "X-axis direction", and/or the thickness direction may refer to the "Z-axis direction". For the reference, in the Cartesian coordinate system in FIG. 2, the 'X' may indicate a width direction of the electronic device 200, and the 'Y' may indicate a longitudinal direction of the electronic device 200. In various embodiments, in connection with the direction in which an element is oriented, in addition to the Cartesian coordinate system illustrated in the drawings, "negative/positive (−/+)" may be mentioned together therewith. For example, a first surface (the front surface) of an electronic device or a housing may refer to "a surface facing the +Z-direction", and a second surface (the rear surface) thereof may refer to "a surface facing the −Z-direction". In connection with the description of directions, when 'negative/positive (−/+)' is not described, it may be interpreted as including both the + direction and the − direction unless otherwise defined. For example, the 'X-axis direction' may be interpreted as including both the +X-direction and the −X-direction. The foregoing is based on the Cartesian coordinate system illustrated in the drawings in order for the sake of brevity of descriptions, and it should be noted that the descriptions of directions or elements do not limit various embodiments of the disclosure.

The electronic device 200 (e.g., the electronic device 101 of FIG. 1) according to various embodiments of the disclosure may be a wearable electronic device capable of being worn on the body of a user. Hereinafter, in describing various embodiments of the disclosure, although a smart watch is described as an example thereof, it should be noted that it is not necessarily limited thereto.

Referring to FIG. 2, the electronic device 200 according to various embodiments of the disclosure may include a housing 210, a bezel 220, and attachment/detachment parts 230.

According to various embodiments, the housing 210 may include a first plate 211 configured to form a first surface 211a facing a first direction and a second plate 215 configured to form a second surface 215a facing a second direction opposite to the first direction. The first surface 211a of the housing 210 may be configured to be open, and a window member 213 may be mounted to form at least a part of the first surface 211a so as to close the open portion of the housing 210. The first surface 211a and the second surface 215a may be formed to be flat, but may at least partially include a curved surface. The second surface 215a of the housing 210 may include a penetration part 217 having a transparent portion such that light generated in an optical element part (e.g., a light-emitting part) disposed inside the housing is emitted to the outside.

According to various embodiments, various kinds of circuit devices, for example, the processor 120 (e.g., an application processor (AP)), the memory 130, the input/output interface 150, and the communication interface 170, which have been described above through FIG. 1, may be accommodated inside the housing 210. In addition, a battery (not shown) may be accommodated inside the housing 210 so as to secure power.

According to various embodiments, the housing 210 may include at least a part made of a metal material. For example, a portion (e.g., the edge) of the housing 210 may be made of a metal material, and the other portion of the housing 210 may be made of a synthetic resin material. According to various embodiments, when a portion of the housing 210 is made of a metal material, the portion may be utilized as an antenna radiator.

According to various embodiments, the window member 213 may be disposed on the first surface 211a of the housing 210. The front surface of the window member 213 may be configured to substantially form a part of the first surface 211a of the housing 210. The window member 213 may be made of a transparent or a translucent material, for example, glass or resin (e.g., acrylic or polycarbonate), and an image or a picture output from a display panel disposed under the window member 213 may be visible through the window member 213. For example, as illustrated in FIG. 2, an analog watch-shaped image output from the display panel may be displayed through the window member 213.

According to various embodiments, the bezel 220 may be disposed on the edge of the window member 213. At this case, the bezel 220 may be coupled to be relatively rotatable with respect to the housing 210. For example, the bezel 220 may be configured to rotate along the edge of the window member 213 such that a user performs various inputs for executing various functions. According to an embodiment, the bezel 220 may be made of a metal material to make the appearance of the electronic device 200 be beautiful, but it may be not limited thereto.

According to various embodiments, the attachment/detachment parts 230 may be arranged to extend and protrude in a direction away from each other from both ends of the housing 210. The attachment/detachment parts 230 may be coupled to a wearable part (not shown) formed to be worn on the wrist of a user. The attachment/detachment parts 230 may be configured to have a binding groove formed therethrough, which is engaged with the wearable part. Various types of wearable parts having various textures (for example, a rubber material, plastic, or metal) may be applied to the wearable part mountable to the electronic device, and the various types of wearable parts may be detached from or attached to the attachment/detachment parts 230 of the electronic device 200 according to a user's preference.

Figure 3:
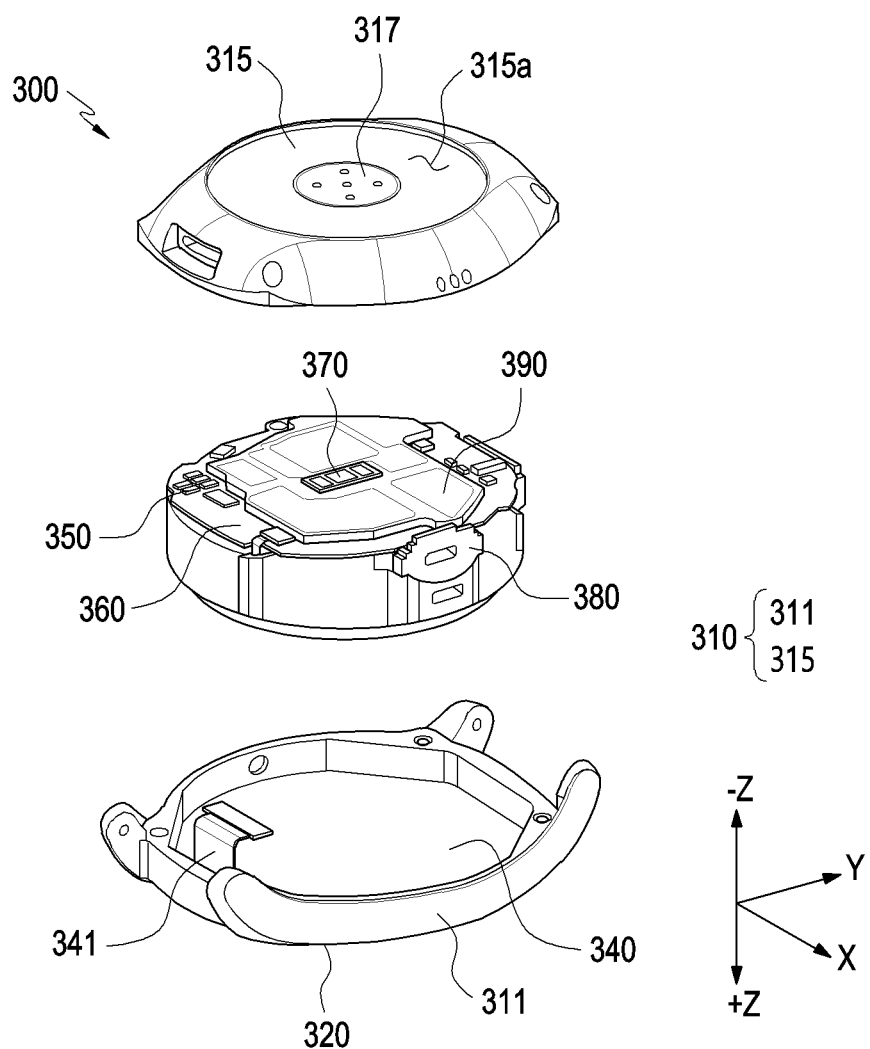
FIG. 3 is an exploded perspective view illustrating an internal structure of an electronic device according to various embodiments.

FIG. 3 is an exploded perspective view showing an internal structure of an electronic device according to various embodiments.

In the Cartesian coordinate system in FIG. 3, the 'X' may indicate the width direction of an electronic device 300, the 'Y' may indicate the longitudinal direction of the electronic device 300, and the 'Z' may indicate the height direction (the thickness direction) of the electronic device 300.

Referring to FIG. 3, the electronic device 300 according to various embodiments may include a housing 310, a bezel 320, a display panel 340, an electronic component 350, a main circuit board 360, a bracket 380, a battery 390, and a sensor 370. In connection with the housing 310 and/or the bezel 320 of the electronic device 300 illustrated in FIG. 3, the description of the housing 210 and/or the bezel 220 illustrated in FIG. 2 may be referred to.

According to various embodiments, the housing 310 may be configured to accommodate various elements such as the display panel 340, the electronic component 350, the main circuit board 360, and/or the sensor 370. The housing 310 may include a space for accommodating various elements. The space may be a space formed by being surrounded by a first plate 311 (e.g., the first plate 211 of FIG. 2) and a second plate 315 (e.g., the second plate 215 of FIG. 2), and may be a portion filled with various elements arranged therein without an empty space except for a predetermined tolerance. According to various embodiments, the housing 310 may be made of a material which allows a wireless signal or a magnetic field to at least partially pass therethrough.

According to various embodiments, the display panel 340 may be disposed in the second direction (the −Z-axis direction) of the window member (e.g., 213 of FIG. 2). For example, the display panel 340 may be coupled to the rear surface of the window member and may be provided in the form of a module together with the window member, but it may be not limited thereto. The display panel 340 may be configured to display image or picture information to the outside through the window member, and may be configured to output an execution screen of various applications (e.g., a game, Internet banking, a schedule management) according to a user's operation.

According to various embodiments, the display panel 340 may include a liquid crystal display (LCD) panel, a light-emitting diode (LED) display panel, an organic light-emitting diode (OLED) display panel, a micro-electromechanical system (MEMS) display panel, an electronic paper display panel, or the like. The electronic device according to various embodiments may be configured to have the display panel 340 and a touch screen panel integrally provided so as to perform a touch screen function. According to various embodiments, an antenna radiator may be disposed on the inner surface or the outer surface of the display panel 340 so as to perform a wireless communication function.

According to various embodiments, the display panel 340 may be disposed inside the housing, and may be electrically connected to a display circuit board 341 configured to be at least partially curved. The display circuit board 341 may be configured to deliver an electrical signal for driving the display panel 340.

According to various embodiments, the main circuit board 360 may be disposed to face the battery 390. Various electronic components including a processor and a communication module may be arranged on the main circuit board 360. In this case, the processor and/or the communication module may be mounted in the form of an integrated circuit chip, but it may not be limited thereto.

According to various embodiments, the electronic component 350 may be disposed on the main circuit board 360, and may include an antenna radiator and/or a wireless charging antenna. The antenna radiator may be configured to transmit and receive radio signals in a magnetic secure transmission (MST) method. For example, the antenna radiator may be an MST antenna. As another example, the antenna radiator may be a near field communication (NFC) antenna transmitting and receiving wireless signals in an NFC method. According to an embodiment, a shielding structure may be disposed around the antenna radiator to block signal interference between other electronic components. The wireless charging antenna may be attached to one surface of the main circuit board 360. The wireless charging antenna may be formed in the form of a flat coil. The wireless charging antenna may be made of a conductive material and may be electrically connected to the main circuit board 360. The wireless charging antenna may be configured to generate a current by electromagnetic induction generated from an external electronic device. The current generated in the wireless charging antenna may be configured to charge the battery (not shown) through the main circuit board 360.

According to various embodiments, the electronic device 300 may further include a heat dissipation structure (not shown). For example, the heat dissipation structure may be disposed between the main circuit board 360 and the battery 390. The heat dissipation structure may be configured receive heat generated in the main circuit board 360 to prevent and/or inhibit the main circuit board 360 from being overheated.

According to various embodiments, the second plate 315, which is configured to form a second surface 315a toward the second direction (the −Z-axis direction) of the housing 310, may include a penetration part 317 at least a portion of which is transparent. The second plate 315 may not be limited to being made of a glass material, and may be made of a transparent material such as transparent reinforced plastic. The second plate 315 may be configured to be in contact with a part (e.g., wrist) of the human body of a user. Referring to FIG. 3, the second plate 315 may have a center area formed as the penetration part 317, which is transparent (or translucent), for a sensing operation of the sensor 370, and the other areas (the peripheral area) other than the center area may be formed to be opaque. According to an embodiment, differently from what is illustrated in drawings, the entire area of the second plate 315 may also be formed to be transparent.

According to various embodiments, the sensor 370 may be disposed between the main circuit board 360 and the second plate 315 so as to sense biometric information of a user. For example, the sensor 370 may be a body temperature sensor for measuring a body temperature when a user wears the electronic device 300. The processor (e.g., the processor 120 of FIG. 1) may be configured to receive an electrical signal from the sensor 370 so as to calculate and determine the body temperature of a user. According to various embodiments, the sensor 370 may be a sensor, alternatively or additionally, further including another function (e.g., a heart rate measurement), in addition to measuring a body temperature. For example, a heart rate monitoring (HRM) device may be integrated into the sensor 370. The sensor 370 including a heart rate monitoring device may be configured to detect vasoconstriction/vasodilation by reflection of light according to a change in blood volume in blood vessels in the skin of a human body. In addition, various other embodiments may be applied to the sensor 370.

Figure 4:
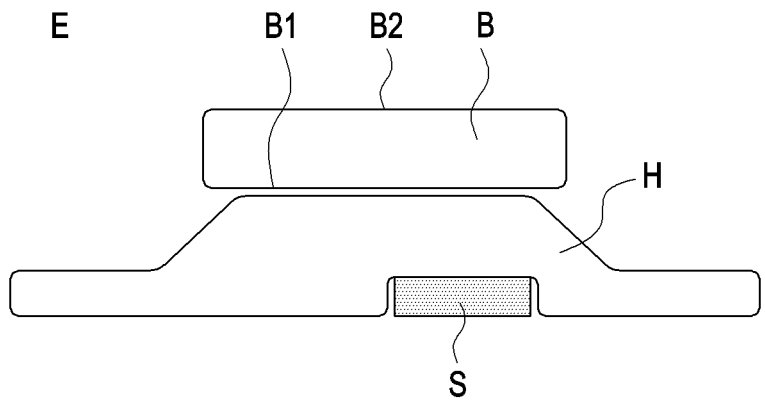
FIG. 4 is a diagram illustrating portions of an electronic device and a human body illustrating a body temperature measurement principle according to various embodiments.

FIG. 4 is a diagram illustrating portions of an electronic device and a human body in order to show a body temperature measurement principle according to various embodiments.

An electronic device including a body temperature sensor S may be configured to measure the body temperature of a user in a state where a part B (e.g., wrist) of the human body of a user is in contact with a housing H of the electronic device. The body temperature sensor S may be disposed in the housing H of the electronic device, for example, on the inner surface of a plate configured to form the exterior of the housing H.

As illustrated in FIG. 4, when a body temperature of a user is measured using the body temperature sensor S, the temperature of a skin surface B1 of the user may be measured, but it may be difficult to measure the temperature of a deep part B2 spaced apart from the skin surface B1 of the user by a predetermined (e.g., specified) distance. In addition, the temperature of the skin surface B1 of the user may be affected by an external environment E. For example, since the temperature of the external environment E is very low in winter, when measured in the winter season, the temperature of the skin surface B1 of the user may be measured lower than the actual body temperature of the user.

Through the various example embodiments illustrated in FIGS. 5, 6, 7, 8, 9, 10 and FIG. 11 described in greater detail below, an electronic device and a body temperature measurement method capable of more accurate measuring a body temperature in various use environments will be described in greater detail.

Figure 5:
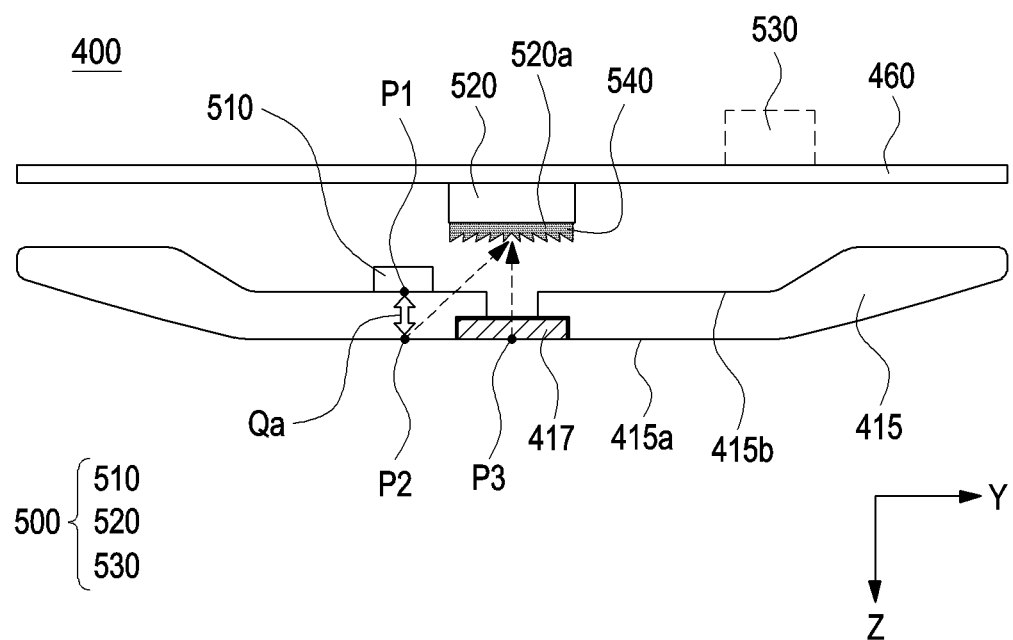
FIG. 5 is a diagram illustrating an internal structure of an electronic device including at least two temperature sensors according to various embodiments.
Figure 6:
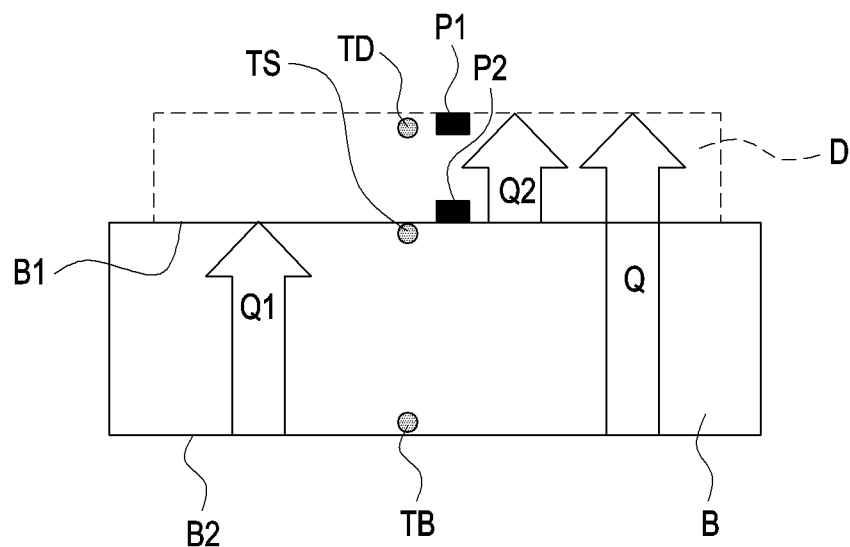
FIG. 6 is a diagram illustrating a body temperature measurement principle according to a heat flow according to various embodiments.

FIG. 5 is a diagram illustrating an example internal structure of an electronic device including at least two temperature sensors according to various embodiments. FIG. 6 is a diagram illustrating a body temperature measurement principle according to a heat flow according to various embodiments.

Referring to FIG. 5, an electronic device 400 according to various embodiments of the disclosure may include a housing, a substrate, a processor, and at least two temperature sensors 500. In connection with the housing, the substrate, and/or the processor of the electronic device 400 illustrated in FIG. 5, descriptions of the housing (e.g., the housing 210 and 310 of FIG. 2 and FIG. 3), the substrate (e.g., the main circuit board 360 of FIG. 3), and/or the processor (e.g., the processor 120 of FIG. 1) according to the above-described embodiments may be referred to.

The at least two temperature sensors 500 may be arranged in the electronic device, and may include a contact-type temperature sensor 510 and a non-contact-type temperature sensor 520 arranged at different positions in the housing. Here, whether the 'contact' or the 'con-contact' may be determined according to whether the sensor can measure a temperature of an object-to-be-measured in a state of being in direct contact therewith or whether the sensor can measure a temperature thereof even in a state of being not in contact therewith. For example, the contact-type temperature sensor 510 may include a thermistor, and the non-contact-type temperature sensor 520 may include an infrared absorber. According to various embodiments, the at least two temperature sensors 500 may further include a third temperature sensor 530 provided separately. The third temperature sensor 530 may be a sensor for measuring a temperature of an external environment (e.g., the external environment E of FIG. 4), and may be additionally provided according to an embodiment. When the third temperature sensor 530 is provided, a body temperature of a user may be corrected based on a temperature of the external environment, which is measured by the third temperature sensor 530. According to various embodiments, in relation to the third temperature sensor 530, the contact-type temperature sensor 510 may be referred to as "the first temperature sensor 510", and the non-contact-type temperature sensor 520 may be referred to as "the second temperature sensor 520". In this case, it should be noted that the 'ordinal number' for each temperature sensor is only for distinguishing between temperature sensors and does not indicate the importance or the priority order of the temperature sensor.

According to various embodiments, the processor (e.g., the processor 120 of FIG. 1) may be configured to define (or decide) a body temperature of a user using the temperature data obtained using the at least two temperature sensors 500.

On the other hand, the processor (e.g., the processor 120 of FIG. 1) may be configured to measure a temperature of a first point P1 on the inner surface of the housing (e.g., a plate) using the contact-type temperature sensor 510, and may be configured to measure a temperature of a second point P2 on the outer surface of the housing (e.g., a plate) using the non-contact-type temperature sensor 520. A heat flow (heat flux) can be monitored using the measured temperature of the first point P1 and the measured temperature of the second point P2, and thus a body temperature of a user can be estimated through same.

FIG. 6 illustrates an example principle for a heat flow according to various embodiments of the disclosure. A total heat flow Q in the system may be the sum of a heat flow Q1 in a first object (e.g., the user's skin B) and a heat flow Q2 in a second object (e.g., the electronic device D). For example, the heat flow Q1 in the user's skin B may be proportional to the difference between a temperature value TS of the skin surface B1 and a temperature value TB of a deep part B2, the heat flow Q2 in the electronic device D may be proportional to the difference between a temperature value TD at the first point P1 and a temperature value at the second point P2 of the electronic device. In this case, the temperature value at the second point P2 of the electronic device may be approximated to the temperature value TS of the skin surface B1. When the temperature value TD at the first point P1 and the temperature value (e.g., the temperature value TS of the skin surface B1) at the second point P2 of the electronic device D are measured, it may be possible to estimate the heat flow Q2 of the electronic device D, and further it may be possible to estimate the value of the heat flow Q1 in the skin or to estimate a change amount thereof. According to various embodiments of the disclosure, when the temperature value TD at the first point P1 and the temperature value (the temperature value TS of the skin surface B1) at the second point P2 of the electronic device D are measured, it may be possible to estimate the heat flow Q2 of the electronic device D, and through same, the value of the heat flow Q1 in the skin or a change amount thereof may be estimated and thus a body temperature of a user may be defined. The measured temperature value TD at the first point P1 and the temperature value (the skin temperature value TS) at the second point P2 may be stored in a memory (e.g., the memory 130 of FIG. 1), and by accumulating same, it may be possible to derive a more accurate measurement result for a body temperature by reflecting same in the case where a body temperature is measured immediately on-demand.

Referring to FIG. 5 again, according to the electronic device 400 according to various embodiments of the disclosure, the processor (e.g., the processor 120 of FIG. 1) may be configured to monitor a heat flow using the contact-type temperature sensor 510 and the non-contact-type temperature sensor 520 as a pair. In this case, one of the pair of temperature sensors 510 and 520 may be disposed adjacent to a plate (e.g., the second plate 415 of FIG. 5) configured to form the exterior of the housing, and the other sensor may be positioned inside the housing. The 'plate' may be an element which is configured to form a part (e.g., the exterior) of the housing and has an inner surface on which at least one sensor is disposed. In the description of FIG. 5 and therebelow, although a second plate 415 is described as an example therefor, it may not be limited thereto. According to an embodiment, it should be noted that the 'plate' corresponds to another element (e.g., the first plate 311 or the bezel 320) other than the second plate 415.

In order to monitor the heat flow, the two sensors 510 and 520 included in the electronic device 400 may be disposed to be spaced apart from each other by a predetermined distance in the height direction (the Z-axis direction) of the electronic device. For example, as illustrated in FIG. 5, the contact-type temperature sensor 510 may be disposed on the inner surface 415b of the second plate 415, and the non-contact-type temperature sensor 520 may be disposed on the substrate 460. For example, a thermistor, which is an example of the contact-type temperature sensor 510, is disposed on the inner surface 415b of the second plate 415, and an infrared absorber as an example of the non-contact-type temperature sensor 520 may be disposed on the substrate 460. In this case, the contact-type temperature sensor 510 and the non-contact-type temperature sensor 520 may be arranged at positions which do not overlap each other in the height direction (the Z-axis direction) of the electronic device. According to an embodiment, the non-contact-type temperature sensor 520 may be disposed to be slightly spaced apart from the contact-type temperature sensor 510 in the height direction (the Z-axis direction) of the electronic device and may also be disposed to be spaced apart therefrom by a predetermined distance in the horizontal direction (e.g., the Y-axis direction), such that the non-contact-type temperature sensor and the contact-type temperature sensor do not overlap each other in the height direction (the Z-axis direction) of the electronic device.

Referring to FIG. 3 and FIG. 5 together, the electronic device 400 including the second plate 415 and the substrate 460 may be configured to have the penetration part 417 formed in the center of the second plate 415, and to have the non-contact-type temperature sensor 520 disposed in the height direction (the Z-axis direction) of the electronic device 400 from the penetration part 417. In addition, the contact-type temperature sensor 510 may be disposed on the inner surface 415b of the second plate 415, which surrounds the penetration part 417.

The processor (e.g., the processor 120 of FIG. 1) may be configured to measure a temperature of the first point P1 positioned on the inner surface 415b of the second plate 415 using the contact-type temperature sensor 510, and may be configured to measure a temperature of the second point P2 positioned on the outer surface 415a of the second plate 415 using the non-contact-type temperature sensor 520. In this case, the contact-type temperature sensor 510 may be configured to detect a temperature of an object-to-be-measured using the properties of heat conduction among various heat transfer methods, and the non-contact-type temperature sensor 520 may be configured to detect a temperature of an object-to-be-measured using the properties of heat radiation. According to an embodiment, the second point P2 may be positioned in the height direction (the Z-axis direction) of the electronic device from the first point P1 in the outer surface 415a of the second plate 415. That is, the processor (e.g., the processor 120 of FIG. 1) may be configured to measure a temperature of the outer surface 415*a* of the second plate 415, which is positioned in the height direction (the Z-axis direction) of the electronic device from the contact-type temperature sensor 510 using the non-contact-type temperature sensor 520. According to an embodiment, the non-contact-type temperature sensor 520 may include an infrared absorber, and using same, may be configured to detect thermal radiation energy of the second plate 415. According to an embodiment, the non-contact-type temperature sensor 520 may be configured to measure a temperature of a third point P3 on the penetration part 417 positioned in the height direction (the Z-axis direction) of the electronic device from the non-contact-type temperature sensor 520. In addition, according to an embodiment of the disclosure, the electronic device 400 may further include a pattern member 540, and thus the processor (e.g., the processor 120 of FIG. 1) may be configured to more easily measure a temperature of a point (e.g., the second point P2) which is not positioned on the non-contact-type temperature sensor 520 and in the height direction (the Z-axis direction) of the electronic device.

According to various embodiments, the pattern member 540 may be disposed on the inner surface 415*b* of the second plate 415 or the surface of the non-contact-type temperature sensor 520. In the embodiment of FIG. 5, it is illustrated that the pattern member 540 is disposed on the surface of the non-contact-type temperature sensor 520, for example, a surface 520*a* of the non-contact-type temperature sensor 520, which faces the second plate 415. The processor (e.g., the processor 120 of FIG. 1), using the non-contact-type temperature sensor 520 according to the embodiment illustrated in FIG. 5, may be configured to measure a temperature of a point (e.g., the third point P3) positioned in the height direction (the Z-axis direction) of the electronic device from the non-contact-type temperature sensor 520, and may be configured to more easily measure a temperature of a point (e.g., the second point P2) which is not positioned in the height direction (the Z-axis direction) of the electronic device. The processor (e.g., the processor 120 of FIG. 1), using the measured temperature of the first point P1 and the measured temperature of the second point P2, may be configured to monitor a heat flow Qa between the outer surface 415*a* and the inner surface 415*b* of the plate 415 and through same, may be configured to estimate a body temperature of a user. The processor (e.g., the processor 120 of FIG. 1) may also be configured to measure a temperature of a user using the non-contact-type temperature sensor 520 immediately on-demand. The contact-type temperature sensor has the characteristic of sensing thermal conductivity, and thus it takes time for the initial measurement thereof. Therefore, it may be disadvantageous in that the contact-type temperature sensor 510 immediately measures a body temperature. On the other hand, since the non-contact-type temperature sensor 520 can measure faster than the contact-type temperature sensor 510, a body temperature of a user can be measured immediately on-demand using the same. Referring to FIG. 5, the processor may be configured to determine a body temperature of a user, based on both accumulated data on the temperature estimated through the monitored heat flow Qa and the real-time temperature data of the third point P3, which is measured through the non-contact-type temperature sensor 520.

In FIG. 5, the distance of spacing between the inner surface 415*b* of the second plate 415 and the substrate 460 is merely conceptually or exaggeratedly illustrated for the convenience of explanation, and the actual distance of spacing may be shorter. For example, the distance of spacing between the inner surface 415*b* of the second plate 415 and the substrate 460 may be 0.5 mm to 5 mm. However, the distance of spacing may not be not limited thereto, and it may be variously configured according to various embodiments with respect to the shape or thickness of a housing of the electronic device 400, the internal structure of a housing, or the arrangement of components such as the arrangement of a substrate. In addition, although it appears that there is an empty space between the inner surface 415*b* of the second plate 415 and the substrate 460 in FIG. 5, according to an embodiment, various electronic components may be arranged inside the electronic device, and thus the empty space may not substantially exist.

Figure 7:
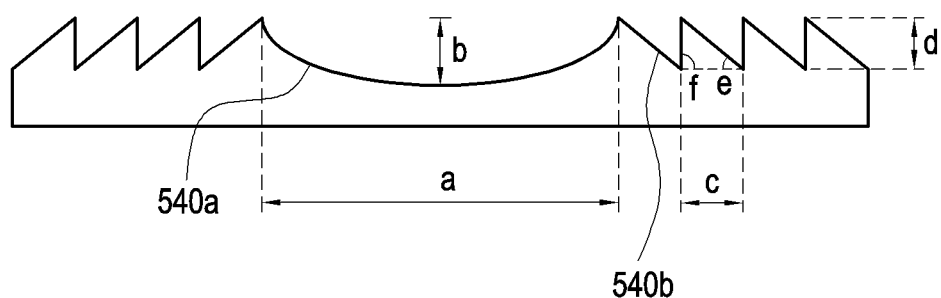
FIG. 7 is a diagram illustrating an example pattern member according to various embodiments.

FIG. 7 is a diagram illustrating an example pattern member 540 according to various embodiments.

According to an embodiment, the pattern member 540 may be applied when a non-contact-type temperature sensor (e.g., the non-contact-type temperature sensor 520 of FIG. 5) and a contact-type temperature sensor (e.g., the contact-type temperature sensor 510 of FIG. 5) are not arranged in the height direction (the Z-axis direction) of the electronic device and are arranged at positions having an angle with respect to the height direction of the electronic device.

Referring to FIG. 7, the pattern member 540 may include an open portion 540*a* in the center thereof and an inclined portion 540*b* around the open portion. The width a and the height b of the open portion 540*a* and the width c and height d of the inclined portion 540*b* may be variously applied according to an embodiment. For example, in various embodiments, the open portion 540*a* may be formed to have the width a of 100-300 μm and the height b of 10-30 μm, and the inclined portion 540*b* may be formed to have the width c of 10-30 μm and the height d 10-40 μm. According to an embodiment, the inclined portion 540*b* may be formed to have a cross section having a triangular pole shape, and angles e and f between the base and other sides adjacent to the base of the inclined portion 540*b* may be formed to have an angle of 20-50° and an angle of 60-85°, respectively. A non-contact-type temperature sensor (e.g., the non-contact-type temperature sensor 520 of FIG. 5) may be configured to detect thermal radiation energy of a heat source (e.g., the third point P3) positioned in the height direction (the Z-axis direction) of the electronic device through the open portion 540*a* in the center of the pattern member 540, and may be configured to detect thermal radiation energy of a heat source (e.g., the second point P2) not positioned in the height direction (the Z-axis direction) of the electronic device through the inclined portion 540*b* therearound. According to various embodiments, as the pattern member 540 includes the open portion 540*a* and the inclined portion 540*b*, if the pattern member is configured to easily measure thermal radiation energy in various directions, the pattern member may have any shape. For example, the pattern member 540 may be in the form of a film or in the form of a sheet, or may be formed to have the form of a lens.

Figure 8:
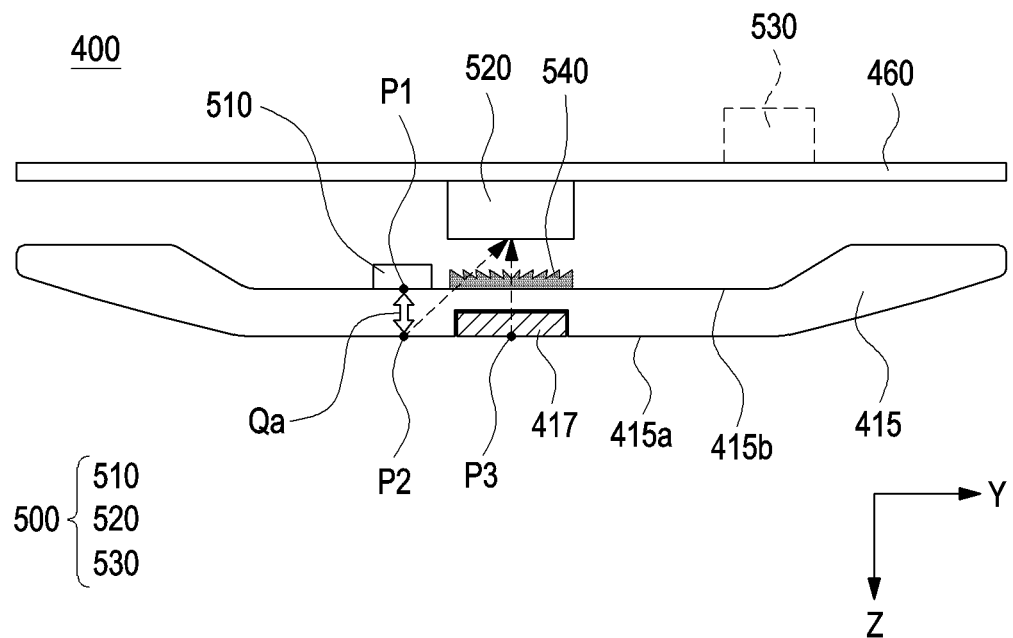
FIG. 8 is a diagram illustrating an internal structure of an electronic device including at least two temperature sensors according to various embodiments.

FIG. 8 is a diagram illustrating an example internal structure of an electronic device including at least two temperature sensors according to various embodiments.

Referring to FIG. 8, the at least two temperature sensors 500 may be arranged in the electronic device, and may include a contact-type temperature sensor 510 and a non-contact-type temperature sensor 520 arranged at different positions in the housing. According to various embodiments, the processor (e.g., the processor 120 of FIG. 1) may be configured to define (or decide) a body temperature of a user using the temperature data obtained using the at least two temperature sensors 500.

The pattern member 540 may be disposed on the inner surface 415b of the second plate 415 or the surface 520a of the non-contact-type temperature sensor 520. In the embodiment of FIG. 8, an embodiment, in which the pattern member 540 is disposed on the inner surface 415b of the second plate 415, is illustrated. According to an embodiment, the pattern member 540 may be disposed on the inner surface 415b of the second plate 415, which is between the penetration part 417 and the non-contact-type temperature sensor 520. In the structure, the non-contact-type temperature sensor 520 may be configured to measure a temperature of a point (e.g., the third point P3) positioned in the height direction (the Z-axis direction) of the electronic device from the non-contact-type temperature sensor 520, and may also be configured to measure a temperature of a point (e.g., the second point P2) which is not positioned in the height direction (the Z-axis direction) of the electronic device.

The processor (e.g., the processor 120 of FIG. 1) may be configured to measure a temperature of the first point P1 positioned on the inner surface 415b of the second plate 415 using the contact-type temperature sensor 510, and may be configured to measure a temperature of the second point P2 positioned on the outer surface 415a of the second plate 415 using the non-contact-type temperature sensor 520. In addition, the processor (e.g., the processor 120 of FIG. 1), using the measured temperature of the first point P1 and the measured temperature of second point P2, may be configured to monitor the heat flow Qa in the housing, and may be configured to estimate a body temperature of a user.

Figure 9:
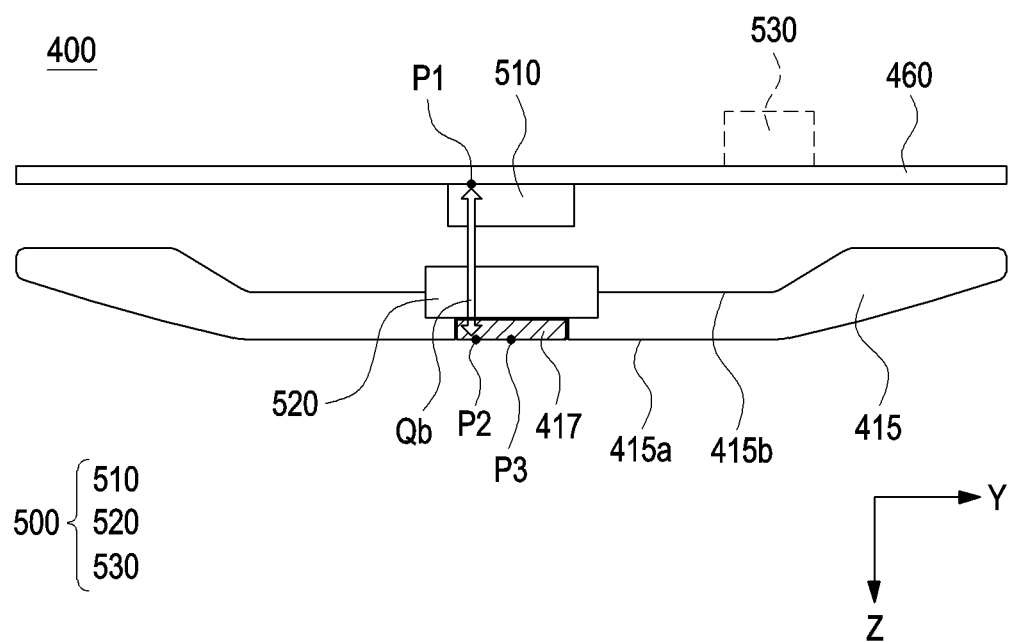
FIG. 9 is a diagram illustrating an internal structure of an electronic device including at least two temperature sensors according to various embodiments.

FIG. 9 is a diagram illustrating an example internal structure of an electronic device including at least two temperature sensors according to various embodiments of the disclosure.

The embodiment illustrated in FIG. 9 may include a contact-type temperature sensor 510 and a non-contact-type temperature sensor 520 arranged at different positions in the housing.

As illustrated in FIG. 9, the electronic device 400 according to an embodiment may have the contact-type temperature sensor 510 disposed on the substrate 460 and the non-contact-type temperature sensor 520 disposed on the inner surface 415b of the second plate 415. For example, a thermistor may be disposed on the substrate 460, and an infrared absorber may be disposed on the inner surface 415b of the second plate 415. In this case, the contact-type temperature sensor 510 and the non-contact-type temperature sensor 520 may be arranged at positions which overlap each other in the height direction (the Z-axis direction) of the electronic device. The non-contact-type temperature sensor 520 and the contact-type temperature sensor 510 may be arranged at positions which overlap each other in the height direction (the Z-axis direction) of the electronic device and are slightly spaced apart in the height direction (the Z-axis direction). The distance of spacing between the inner surface 415b of the second plate 415 and the substrate 460 may be 0.5 mm to 5 mm, and in this case, the distance between the non-contact-type temperature sensor 520 and the contact-type temperature sensor 510 may be formed to be shorter than the distance of spacing between the inner surface 415b of the second plate 415 and the substrate 460. However, the distance of spacing may not be not limited thereto, and it may be variously configured according to various embodiments with respect to the shape or the thickness of a housing of the electronic device 400, the internal structure of a housing, or the arrangement of components such as the arrangement of a substrate.

A temperature of the first point P1 may be measured using the contact-type temperature sensor 510. In addition, a temperature of the second point P2 may be measured using the non-contact-type temperature sensor 520. In the embodiment of FIG. 9, the non-contact-type temperature sensor 520 may be disposed in the height direction (the Z-axis direction) of the electronic device from the second point P2, and thus a temperature of the second point P2, which spaced apart from the contact-type temperature sensor 510 in the height direction (Z-axis direction) of the electronic device, may be measured even without a separate pattern member (e.g., the pattern member 540 of FIG. 5 and FIG. 8).

The processor (e.g., the processor 120 of FIG. 1) may be configured to measure a temperature of the first point P1 inside the housing through the contact-type temperature sensor 510, and may be configured to measure a temperature of the second point P2 on the outer surface 415a of the second plate 415 through the non-contact-type temperature sensor 520. In addition, the processor (e.g., the processor 120 of FIG. 1), using the measured temperature of the first point P1 and the measured temperature of second point P2, may be configured to monitor a heat flow Qb, and through same, may be configured to estimate a body temperature of a user. According to various embodiments, the processor may also be configured to determine a body temperature of a user, based on both accumulated data on the temperature estimated through the monitoring of the heat flow Qb and the real-time data in which a temperature of the third point P3 is measured immediately on-demand through the non-contact-type temperature sensor 520.

Figure 10:
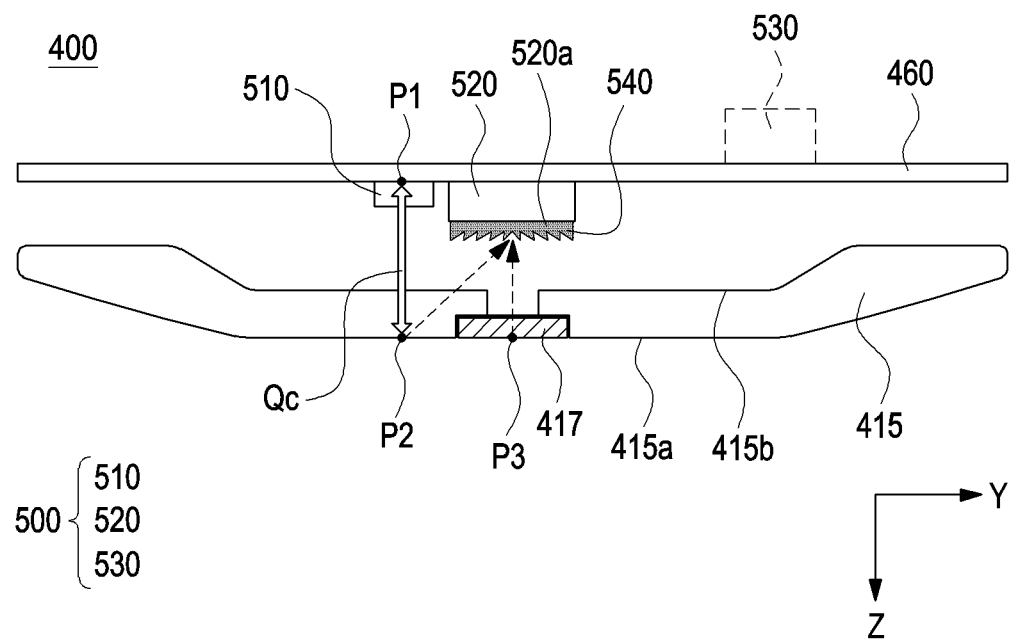
FIG. 10 is a diagram illustrating an internal structure of an electronic device including at least two temperature sensors according to various embodiments.

FIG. 10 is a diagram illustrating an example internal structure of an electronic device including at least two temperature sensors according to various embodiments.

The embodiment illustrated in FIG. 10 may include a contact-type temperature sensor 510 and a non-contact-type temperature sensor 520 arranged at different positions in the housing.

According to an embodiment, as illustrated in FIG. 10, both the contact-type temperature sensor 510 and the non-contact-type temperature sensor 520 may be disposed on the substrate 460. For example, both a thermistor and an infrared absorber may be disposed on the substrate 460. In this case, the contact-type temperature sensor 510 and the non-contact-type temperature sensor 520 may be arranged at positions which are slightly spaced apart in the horizontal direction (e.g., the Y-axis direction) on the substrate 460.

The processor (e.g., the processor 120 of FIG. 1) may be configured to measure a temperature of the first point P1 inside the housing using the contact-type temperature sensor 510, and may be configured to measure a temperature of the second point P2 on the outer surface 415a of the second plate 415 using the non-contact-type temperature sensor 520. In addition, the processor (e.g., the processor 120 of FIG. 1), using the measured temperature of the first point P1 and the measured temperature of second point P2, may be configured to monitor a heat flow Qc in the housing, and may be configured to estimate a body temperature of a user. The electronic device 400 may further include the pattern member 540 disposed on the surface 520a of the non-contact-type temperature sensor 520, and thus may be configured to easily measure a temperature of a point (e.g., second point P2) which is not positioned on the non-contact-type temperature sensor 520 and on the Z-axis.

The processor (e.g., the processor 120 of FIG. 1) may be configured to measure a temperature of the first point P1 through the contact-type temperature sensor 510 and a temperature of the second point P2 through the non-contact-type temperature sensor 520, so as to monitor the heat flow Qc using the measured temperature of the first point P1 and the measured temperature of the second point P2, and through same, to estimate a body temperature of a user. According to various embodiments, the processor (e.g., the processor 120 of FIG. 1) may also be configured to determine a body temperature of a user, based on both accumulated data on the temperature estimated through the monitoring of the heat flow Qc and the real-time data in which a temperature of the third point P3 is measured immediately on-demand through the non-contact-type temperature sensor 520.

In the embodiment of FIG. 10, the distance between the first point P1 and the second point P2, which is the measurement standard for the distance of the heat flow Q, may be formed to be relatively long.

Accordingly, it may possible to more accurately measure a body temperature.

Figure 11:
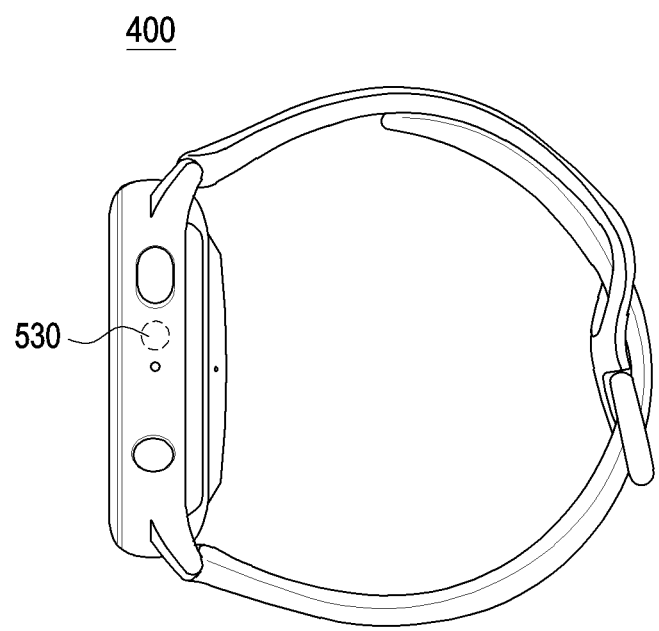
FIG. 11 is a diagram illustrating a position of a third temperature sensor according to various embodiments.

FIG. 11 is a perspective view showing the position of a third temperature sensor 530 according to various embodiments.

In the embodiments of FIG. 5, FIG. 8, FIG. 9, and FIG. 10 described above, an embodiment, in which the third temperature sensor 530 is disposed on a substrate 460, is shown. However, the position of the third temperature sensor 530 may not be limited to any specific arrangement. According to an embodiment, the third temperature sensor 530 may be disposed adjacent to the housing of the electronic device 400 so as to easily measure a temperature of the external environment E. For example, as illustrated in FIG. 11, the third temperature sensor 530 may be disposed at the lower end of an input device (e.g., a key or a button) positioned on the side surface of the electronic device 400. In addition, for example, the third temperature sensor 530 may be disposed adjacent to a side metal frame (e.g., the first plate 311 of FIG. 3) having high thermal conductivity in the electronic device 400. As described above, the third temperature sensor 530 may be configured to have various positions.

As described above, since the third temperature sensor 530 according to various embodiments may be provided, the processor (e.g., processor 120 of FIG. 1) may be configured to compensate the temperature measured using the contact-type temperature sensor 510 and the non-contact-type temperature sensor 520 and thus to more precisely define (or decide) a body temperature of a user.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B", "at least one of A and B", "at least one of A or B", "A, B, or C", "at least one of A, B, and C", and "at least one of A, B, or C", may include any one of, or all possible combinations of the items enumerated together in a corresponding one of the phrases. As used herein, such terms as "1st" and "2nd", or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with", "coupled to", "connected with", or "connected to" another element (e.g., a second element), the element may be coupled with the other element directly (e.g., wiredly), wirelessly, or via a third element.

As used in connection with various embodiments of the disclosure, the term "module" may include a unit implemented in hardware, software, or firmware, or any combination thereof, and may interchangeably be used with other terms, for example, "logic", "logic block", "part", or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to various example embodiments of the disclosure, a wearable electronic device (e.g., the wearable electronic device 400 of FIG. 5) comprises: a housing comprising a first plate (e.g., the first plate 311 of FIG. 3) including a first surface facing in a first direction, and a second plate (e.g., the second plate 315 of FIG. 3 and the second plate 415 of FIG. 5) including a second surface facing a second direction opposite to the first direction; a substrate (e.g., the substrate 460 of FIG. 5) disposed in a space between the first plate and the second plate of the housing; a processor (e.g., the processor 120 of FIG. 1); and at least two temperature sensors (e.g., the temperature sensor 500 of FIG. 5, FIG. 8, FIG. 9, and FIG. 10), wherein the at least two temperature sensors may include a contact-type temperature sensor (e.g., the contact-type temperature sensor 510 of FIG. 5, FIG. 8, FIG. 9, and FIG. 10) and a non-contact-type temperature sensor (e.g., the non-contact-type temperature sensor 520 of FIG. 5, FIG. 8, FIG. 9, and FIG. 10) arranged at positions different from each other in the housing, and wherein the processor may be configured to: determine a body temperature using the temperatures measured by the contact-type temperature sensor and the non-contact-type temperature sensor.

According to various example embodiments, the contact-type temperature sensor may include a thermistor, and the non-contact-type temperature sensor may include an infrared absorber.

According to various example embodiments, the processor may be configured to: measure a temperature of a first point through the contact-type temperature sensor, measure a temperature of a second point through the non-contact-type temperature sensor, and estimate a body temperature based on heat flow information using the measured temperature of the first point and the measured temperature of the second point.

According to various example embodiments, the first point and the second point may be spaced apart from each other by a specified distance in the first direction or the second direction According to various example embodiments, the processor may be configured to determine a body temperature, based on both accumulated data on a temperature estimated using the monitoring of the heat flow information and real-time data immediately measured through the non-contact-type temperature sensor.

According to various example embodiments, the at least two temperature sensors may further include a third temperature sensor (e.g., the third temperature sensor 530 of FIG. 5, FIG. 8, FIG. 9, FIG. 10 and FIG. 11) configured to measure a temperature of an external environment.

According to various example embodiments, the processor may be configured to determine a body temperature through data corrected based on a temperature of the external environment measured using the third temperature sensor.

According to various example embodiments, a pattern portion (e.g., the pattern member 540 of FIG. 5, FIG. 7, FIG. 8, and FIG. 10 disposed on an inner surface of the second plate or on a surface of the non-contact-type temperature sensor, may be included.

According to various example embodiments, the pattern portion may be applied based on the non-contact-type temperature sensor and the contact-type temperature sensor being spaced apart in the first direction or the second direction, and do not overlap each other, and a pattern of the pattern member may include an open portion in a center thereof and an inclined portion around the open portion.

According to various example embodiments, the second plate may include an infrared-transmittable material.

According to various example embodiments, the contact-type temperature sensor may be disposed on an inner surface of the second plate, and the non-contact-type temperature sensor may be disposed on the substrate (see, e.g., FIG. 5 and FIG. 8).

According to various example embodiments, the contact-type temperature sensor may be disposed on the substrate, and the non-contact-type temperature sensor may be disposed on an inner surface of the second plate (see, e.g., FIG. 9).

According to various example embodiments, the contact-type temperature sensor and the non-contact-type temperature sensor may be arranged on the substrate (see FIG. 10).

According to various example embodiments of the disclosure, a method for measuring a body temperature using a wearable electronic device including a contact-type temperature sensor and a non-contact-type temperature sensor, the method may include: measuring a temperature of a first point using the contact-type temperature sensor and measuring, using the non-contact-type temperature sensor, a temperature of a second point disposed to be spaced apart from the first point by a specified distance in the height direction of the wearable electronic device, to monitor a heat flow information; and determining a body temperature, based on both accumulated data on a temperature estimated through monitoring the heat flow information and temperature data immediately measured through the non-contact-type temperature sensor.

According to various example embodiments, the wearable electronic device may further include a third temperature sensor configured to measure a temperature of an external environment, and the determining the body temperature may further include correcting a body temperature, based on a temperature of the external environment measured by the third temperature sensor.

According to various example embodiments a an electronic device may include: a housing; a substrate (e.g., the substrate 460 of FIG. 5) disposed inside the housing; a processor (e.g., the processor 120 of FIG. 1); and at least two temperature sensors (e.g., the temperature sensor 500 of FIG. 5, FIG. 8, FIG. 9, and FIG. 10), wherein the at least two temperature sensors may include a contact-type temperature sensor (e.g., the contact-type temperature sensor 510 of FIG. 5, FIG. 8, FIG. 9, and FIG. 10) and a non-contact-type temperature sensor (e.g., the non-contact-type temperature sensor 520 of FIG. 5, FIG. 8, FIG. 9, and FIG. 10) arranged at positions different from each other in the housing, and the processor may be configured to determine a body temperature using the temperatures the contact-type temperature sensor and the non-contact-type temperature sensor.

According to various example embodiments, the contact-type temperature sensor may include a thermistor, and the non-contact-type temperature sensor may include an infra-red absorber.

According to various embodiments, the processor may be configured to: measure a temperature of a first point through the contact-type temperature sensor, measure a temperature of a second point through the non-contact-type temperature sensor, based on heat flow information using the measured temperature of the first point and the measured temperature of the second point.

According to various example embodiments, the first point and the second point may be spaced apart from each other by a specified distance in the first direction or the second direction According to various example embodiments, the processor may be configured to determine a body temperature, based on both accumulated data on a temperature estimated using the heat flow information and real-time data immediately measured through the non-contact-type temperature sensor.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. A wearable electronic device comprising:
    a housing comprising a first plate including a first surface forming an exterior surface of the wearable electronic device;
    at least one processor;
    memory; and
    at least two temperature sensors, including a contact-type temperature sensor and a non-contact-type temperature sensor including an IR emitter,
    wherein the contact-type temperature sensor is disposed at a portion of the housing, and is configured to measure a first temperature of the portion of the housing,
    wherein the non-contact-type temperature sensor is configured to emit IR light to an area of the first surface to measure a second temperature of the area, wherein the area of the first surface corresponds to the portion of the housing, and
    wherein the memory stores instructions that, when executed by the at least one processor individually or collectively, cause the wearable electronic device to:
        identify information on a heat flow based on the first temperature and the second temperature during a specific period, and
        determine a current body temperature based at least on the information on the heat flow during the specific period.

2. The wearable electronic device of claim 1, wherein the contact-type temperature sensor comprises a thermistor, and the non-contact-type temperature sensor comprises an IR absorber.

3. The wearable electronic device of claim 1, wherein the memory further stores instructions that, when executed by the at least one processor individually or collectively, cause the wearable electronic device to estimate the current body temperature based on information on the heat flow using the first temperature at a first point and the second temperature at a second point.

4. The wearable electronic device of claim 3, wherein the first point and the second point are spaced apart from each other by a distance in a first direction.

5. The wearable electronic device of claim 3, wherein the memory further stores instructions that, when executed by the at least one processor individually or collectively, cause the wearable electronic device to:
    measure, using the non-contact-type temperature sensor, a third temperature of the user by emitting IR light by the IR emitter toward a skin of the user through a transparent window of the housing; and
    determine the current body temperature based at least on the information on the heat flow during the specific period and the third temperature.

6. The wearable electronic device of claim 1, wherein the at least two temperature sensors further comprise a third temperature sensor configured to measure a temperature of an external environment.

7. The wearable electronic device of claim 6, wherein the memory further stores instructions that, when executed by the at least one processor individually or collectively, cause the wearable electronic device to: determine the current body temperature through data corrected based on the temperature of the external environment measured using the third temperature sensor.

8. The wearable electronic device of claim 1, further comprising:
    a second plate including a second surface facing a second direction opposite to a first direction where the first plate faces;
    a substrate disposed in a space between the first plate and the second plate of the housing; and
    a pattern layer disposed on an inner surface of the second plate or a surface of the non-contact-type temperature sensor.

9. The wearable electronic device of claim 8, wherein the pattern layer is applied based on the non-contact-type temperature sensor and the contact-type temperature sensor being spaced apart in the first direction or the second direction, and do not overlap each other, and
    wherein a pattern of the pattern layer comprises an open portion in a center thereof and an inclined portion around the open portion.

10. The wearable electronic device of claim 8, wherein the second plate comprises an infrared-transmittable material.

11. The wearable electronic device of claim 8, wherein the contact-type temperature sensor is disposed on an inner surface of the second plate, and
    the non-contact-type temperature sensor is disposed on the substrate.

12. The wearable electronic device of claim 8, wherein the contact-type temperature sensor is disposed on the substrate, and
    the non-contact-type temperature sensor is disposed on a surface of the second plate.

13. The wearable electronic device of claim 8, wherein the contact-type temperature sensor and the non-contact-type temperature sensor are arranged on the substrate.

14. A method of a wearable electronic device for measuring a body temperature of a user wearing the wearable electronic device comprising a contact-type temperature sensor and a non-contact-type temperature sensor including an IR emitter, the method comprising:

measuring a first temperature of a portion of a housing of the wearable electronic device using the contact-type temperature sensor disposed at the portion of the housing;

measuring, using the non-contact-type temperature sensor, a second temperature of an area of an exterior surface of the wearable electronic device by emitting IR light by the IR emitter to the area, wherein the area of the exterior surface corresponds to the portion of the housing;

identifying information on a heat flow based on the first temperature and the second temperature during a specific period, measuring, using the non-contact-type temperature sensor, a third temperature of the user by emitting IR light by the IR emitter toward a skin of the user through a transparent window of the housing; and determining a current body temperature based at least on the information on the heat flow during the specific period and the third temperature.

15. The method of claim 14, wherein the wearable electronic device further comprises a third temperature sensor configured to measure a temperature of an external environment, and the determining the body temperature further comprises correcting the body temperature based on a temperature of the external environment measured by the third temperature sensor.

16. A wearable electronic device comprising:

a housing comprising a first plate including a first surface forming an exterior surface of the wearable electronic device;

at least one processor;

memory; and at least two temperature sensors, including a contact-type temperature sensor and a non-contact-type temperature sensor including a IR emitter, wherein the contact-type temperature sensor is disposed at a portion of the housing, and is configured to measure a first temperature of the portion of the housing, wherein the non-contact-type temperature sensor configured to emit IR light to an area of the first surface to measure a second temperature of the area, wherein the area of the first surface corresponds to the portion of the housing, and wherein the memory stores instructions that, when executed by the at least one processor individually or collectively, cause the wearable electronic device to:

identify information on a heat flow based on the first temperature and the second temperature during a specific period, and measuring, using the non-contact-type temperature sensor, a third temperature of the user by emitting IR light by the IR emitter toward a skin of the user through a transparent window of the housing; and determine a current body temperature based at least on the information on the heat flow during the specific period and the third temperature.

17. The wearable electronic device of claim 16, wherein the contact-type temperature sensor comprises a thermistor, and the non-contact-type temperature sensor comprises an IR absorber.

18. The wearable electronic device of claim 16, wherein the memory further stores instructions that, when executed by the at least one processor individually or collectively, cause the wearable electronic device to estimate the current body temperature based on information on the heat flow using the first temperature at a first point and the second temperature of the at a second point.

19. The wearable electronic device of claim 18, wherein the first point and the second point are spaced apart from each other by a distance in a first direction.

20. The wearable electronic device of claim 18, wherein the memory further stores instructions that, when executed by the at least one processor individually or collectively, cause the wearable electronic device to determine the current body temperature, based on both accumulated data on a temperature estimated using the information on the heat flow and real-time temperature data immediately measured through the non-contact-type temperature sensor using the third temperature at a third point.

* * * * *